United States Patent [19]

Heather

[11] Patent Number: 4,740,623
[45] Date of Patent: Apr. 26, 1988

[54] METHOD FOR PREPARATION OF BENZYL MERCAPTAN

[75] Inventor: James B. Heather, Hercules, Calif.

[73] Assignee: Stauffer Chemical Company, Westport, Conn.

[21] Appl. No.: 9,844

[22] Filed: Jan. 30, 1987

[51] Int. Cl.$^4$ .......................................... C07C 148/00
[52] U.S. Cl. ...................................................... 568/68
[58] Field of Search ........................................ 568/68

[56] References Cited

U.S. PATENT DOCUMENTS

| | | | |
|---|---|---|---|
| 1,842,414 | 1/1932 | Leaper | 568/68 |
| 2,456,588 | 12/1948 | Loverde | 568/68 |
| 4,082,790 | 4/1978 | Speier | 568/61 |

OTHER PUBLICATIONS

W. Hoffman et al, J. Amer. Chem. Soc., vol. 45, p. 1833 (1923).

*Primary Examiner*—Mary E. Ceperley
*Attorney, Agent, or Firm*—Paul R. Martin

[57] ABSTRACT

A method for the preparation of benzyl mercaptan is disclosed which comprises reacting a benzyl halide of the formula

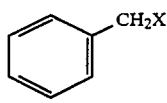

wherein X is chlorine or bromine, with an alkali metal hydrosulfide salt, at a temperature and for a sufficient period of time to cause formation of the benzyl mercaptan, said reaction being conducted under a hydrogen sulfide atmosphere at a temperature of about 50° C. until approximately 90% of the starting material is converted to the benzyl mercaptan, then increasing the temperature to about 80° C. for the balance of the reaction, the initial concentration of said hydrosulfide salt in solution being between about 5% and about 30% by weight.

6 Claims, No Drawings

METHOD FOR PREPARATION OF BENZYL MERCAPTAN

BACKGROUND OF THE INVENTION

The present invention is related to a method for the preparation of benzyl mercaptan, an intermediate compound used in the preparation of S-benzyl thiolcarbamates, compounds which are known as herbicides.

THE PRIOR ART

There are various methods of making benzyl mercaptan which is disclosed in the prior art. One such method, as disclosed in U.S. Pat. No. 4,082,790, comprises reacting an aliphatic chloride or bromide with a mixture of $H_2S$ and ammonia or an amine at a temperature of 0° to 175° C. under autogenous pressure. This reaction can be carried out neat or in the presence of a polar solvent such as methanol, isopropanol, or the like.

Another method disclosed in the prior art (J. A. C. S., Vol. XLV, 1923, p. 1833, W. S. Hoffman et al.) comprises melting a quantity of crystallized sodium sulfide and saturating this with hydrogen sulfide. To this is added an equal volume of ethyl alcohol and the reaction mixture is resaturated with the hydrogen sulfide. Finally, a quantity of benzyl chloride dissolved in alcohol is added. The mixture is allowed to stand in the cold, with frequent shaking for 4 days, and kept cold to prevent as much as possible the oxidation of the mercaptan to the disulfide and the formation of the monosulfide, which, it is disclosed, takes place readily at high temperatures.

A conventional process for making benzyl mercaptan, as disclosed in U.S. Pat. No. 1,842,414, is to react benzyl chloride with sodium hydrosulfide to form benzyl mercaptan plus sodium chloride, in accordance with the following equation.

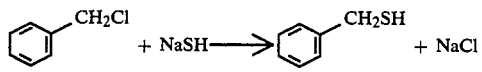

A problem which occurs in this reaction, however, is that significant quantities of benzyl sulfide are produced as a by-product. This reduces the yield of benzyl mercaptan and increases the need for purification of the product which is produced. It would be advantageous, therefore, to find a process for the production of benzyl mercaptan which minimizes the quantity of benzyl sulfide by-product formed during the reaction and optimizes the percent yield of the desired benzyl mercaptan obtained. This invention is concerned with such a process.

DESCRIPTION OF THE INVENTION

A process for the preparation of benzyl mercaptan has now been discovered which comprises reacting a benzyl halide of the formula

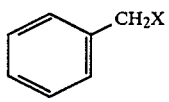

wherein X is chlorine or bromine, with an alkali metal hydrosulfide salt, at a temperature and for a sufficient period of time to cause formation of benzyl mercaptan, said reaction being conducted under a hydrogen sulfide atmosphere at a temperature of about 50° C. until approximately 90% of the starting material is converted to the benzyl mercaptan, then increasing the temperature to about 80° C. for the balance of the reaction, the initial concentration of said hydrogen sulfide salt in solution being between about 5% and about 30% by weight.

The preferred benzyl halide for use in the process of the invention is benzyl chloride. Benzyl bromide can be used, but it is more expensive than benzyl chloride.

The preferred alkali metal hydrosulfide salt is the sodium salt. Other salts which can be used include the potassium salt.

The process as described above results in benzyl mercaptan of high purity and yield being obtained.

There are three elements in the above-described process which are essential to the practice of this invention.

The first has to do with the temperature adjustments carried out during the period of the reaction. Although conducting the reaction of lower temperatures leads to reduced levels of benzyl sulfide impurity, the reaction time becomes excessive. It has been found that maintaining a moderate reaction temperature of about 50° C. until the reaction is about 90% complete, then increasing the temperature to about 80° C. for the balance of the reaction, retains to a substantial degree the advantage of low benzyl sulfide impurity formation while at the same time bringing about rapid completion of the reaction. Under these conditions, the level of unreacted benzyl chloride can be reduced to a ow level without appreciably increasing the benzyl sulfide level.

The effects of the reaction temperature on benzyl sulfide by-product content in the benzyl mercaptan product are shown in the Table below, wherein a series of runs are tabulated. In each of these reactions, the reactants were benzyl chloride and sodium hydrosulfide.

TABLE I

| Reaction Temperature Effects* | | | | | |
|---|---|---|---|---|---|
| Product Composition (gc area %) | | | Temperature Program | | |
| | | | | to % | |
| BzCl | BzSH | Bz₂S | Initial | Completion | Final |
| 0.2 | 96.7 | 1.0 | 50° | 90% | 80° |
| 0.2 | 96.0 | 1.5 | 60° | 90% | 80° |
| 0.1 | 96.7 | 1.8 | 70° | 90% | 80° |
| 0.2 | 96.7 | 1.5 | 50° | 75% | 80° |
| 0.3 | 96.2 | 1.8 | 50° | 60% | 80° |

*All reactions used 1.3 equivalents of 10% aqueous sodium hydrosulfide and 0.2 equivalents of hydrochloric acid under nitrogen (static).
BzCl = benzyl chloride
BzSH = benzyl mercaptan
Bz₂S = benzyl sulfide The Table indicates the initial temperature of the reaction, as well as the ultimate final temperature. As seen from the Table, the best result in terms of high product quality is obtained by conducting the reaction at 50° C. to 90% completion, then raising the temperature to 80° C. for the balance of reaction. Under these conditions, approximately 97 weight percent pure product was obtained upon cooling and phase separation.

Another critical factor in carrying out the process of the invention is to conduct the reaction in the presence of a hydrogen sulfide atmosphere. The hydrogen sulfide atmosphere should be a static hydrogen sulfide atmosphere, which can be maintained by adding a strong acid (such as HCl) to the reaction solution. This strong acid results in a hydrogen sulfide gas being generated, which is effective in maintaining a hydrogen sulfide atmosphere over the reaction solution. The atmosphere does not have to be 100% hydrogen sulfide. What is required is that there be sufficient $H_2S$ in the atmosphere to inhibit the decomposition of sodium hydrosulfide, thus minimizing the amount of by-products formed, described by the following equation:

$$2NaSH \rightleftharpoons Na_2S + H_2S$$

Still another critical factor in carrying out the process of the invention to obtain maximum yield is to provide a sufficient quantity of hydrosulfide salt so that it is initially present in solution at approximately 15% concentration by weight. Although reactions conducted at 5% to about 30% concentration give reasonable reaction times, a reaction time of approximately 6 hours can be obtained using 15% by weight hydrosulfide salt solutions. Higher concentrations of hydrosulfide salt extend the reaction time by a factor of 3 or more.

Over the course of the reaction the quantity of hydrosulfide salt will diminish. However, the starting amount of the compound should be in the range indicated above, 5 to 30%.

The criticality of the hydrosulfide salt concentration in the solution is demonstrated in accordance with the following Table, which represents a series of reactions which were conducted at various sodium hydrosulfide concentrations.

As will be seen from this Table, the optimum concentration of sodium hydrosulfide in solution is about 15%.

TABLE II

Reaction of Benzyl Chloride with Sodium Hydrosulfide (NaSH) Effect of NaSH Concentration*

| Run No. | Conc. | Rxn. Temp. (°C.) | Rxn. Time (hr) | BzCl | BzSH | $Bz_2S$ | Atmosphere |
|---|---|---|---|---|---|---|---|
| 1 | 10% | 85 | 2 | 0.1 | 92.5 | 4.5 | $H_2S$ |
| 2 | 30% | 88 | 16 | 0.5 | 90.2 | 6.0 | $H_2S$ |
| 3 | 45% | 95 | 6 | 94.6 | 0.5 | — | $H_2S^a$ |
| 4 | 10% | 50 | 7 | 0.2 | 98.0 | 0.9 | $H_2S$ |
| 5 | 15% | 50/80 | 11 | 0.0 | 98.0 | 0.9 | $H_2S$ |
| 6 | 20% | 50/80 | 16 | 0.3 | 97.9 | 0.5 | $H_2S$ |
| 7 | 20% | 50/80 | 16 | 0.1 | 97.8 | 0.7 | $H_2S^b$ |
| 8 | 10% | 50/80 | 4 | 0.1 | 98.0 | 0.9 | $N_2^c$ |
| 9 | 15% | 50/80 | 6 | 0.2 | 97.9 | 0.9 | $N_2^c$ |
| 10 | 15% | 50/80 | 5 | 0.2 | 97.4 | 1.0 | $N_2$ |
| 11 | 15% | 50/80 | 5 | 0.2 | 97.7 | 0.8 | $H_2S$ |

Prod. Composition (gc area %) columns: BzCl, BzSH, $Bz_2S$ $^a$Reaction conducted at 50–134 psig.
$^b$Reaction conducted with ultrasound.
$^c$Reaction conducted under a static nitrogen atmosphere with hydrogen sulfide provided by the addition of 0.2 equivalents of hydrochloride acid.
*The mole ratio of NaSH to BzCL was 1.2 to 1 for Runs 1–7, and 1.1 to 1 for Runs 8–11.
BzCl = benzyl chloride
BzSH = benzyl mercaptan
$Bz_2S$ = benzyl sulfide The reaction of the benzyl halide, preferably benzyl chloride, and hydrosulfide salt, preferably sodium hydrosulfide, is preferably carried out in an aqueous system. Other solvents can be added, such as methanol, toluene or glycerol. However, these organic solvents tend to slow the reaction rate, and/or to increase the level of benzyl sulfide impurity in the product.

In general, an excess of sodium hydrosulfide is used to react with benzyl chloride in the process of the invention. Sodium hydrosulfide can be prepared by adding hydrogen sulfide to a sodium hydroxide solution or can be purchased commercially. As previously indicated, a strong acid, such as aqueous hydrochloric acid, can be used to produce the hydrogen sulfide atmosphere, by adding the acid to the slightly larger excess of sodium hydrosulfide in solution.

Preferably, about 0.2 equivalents of hydrochloric acid and 1.3 equivalents of sodium hydrosulfide per equivalent of BzCl results in substantially complete conversion being obtained.

The acid can also serve to adjust the pH of the solution to insure that the minimum amount of disodium sulfide is present. Desirably, the pH of the solution should be about 8. Commercial sodium hydrosulfide preparations conventionally have a pH of about 12. Thus, if a commercial sodium hydrosulfide is incorporated into the reaction mixture, the pH should be adjusted downward with the use of the strong acid or by stirring under a hydrogen sulfide atmosphere.

This invention will be more fully understood by reference to the following examples, which are intended to be illustrative of the method of the invention, but not limiting thereof.

EXAMPLE 1

Preparation of Benzyl Mercaptan

A 500 ml flask with a bottom take-off valve was fitted with a mechanical stirrer, a thermometer, a glass inlet tube, an addition funnel and a rubber septum. The glass inlet tube was connected with a "T" to a nitrogen source and a caustic scrubber. A 45.7% solution of aqueous sodium hydrosulfide (49 ml, 64 g, 0.52 mole) and water (159 ml) were added, and the system was placed under a nitrogen atmosphere. While stirring mechanically at 360 rpm and maintaining a static nitrogen atmosphere, concentrated hydrochloric acid was added (7.5 ml, 0.08 mole), followed by benzyl chloride (46 ml, 0.40 mole). The hydrochloric acid generated the production of an $H_2S$ gas. After heating and stirring the two-phase system at 50° C. for approximately 5 hours, gas chromatography analysis showed 7.2% benzyl chloride, 90.7% benzyl mercaptan, 0.7% benzyl sulfide, and 0.7% benzyl disulfide. The temperature of the solution was then increased to 80° C., and the reaction was continued for an additional 1.5 hours.

The reaction solution was then cooled, purged with nitrogen and allowed to phase separate. The lower organic phase was separated to give, as identified by gas chromatography, 44.0 g of technical benzyl mercaptan (88.6% of theory) which was 97.4 weight percent pure with 0.2 area percent benzyl chloride, 0.9% benzyl sulfide, 0.4% benzyl disulfide and 0.2% of an unidentified isomer of bibenzyl.

EXAMPLE 2

Pilot Plant Demonstration

A 200 gallon, glass-lined Pfaudler reactor was charged with 735 pounds of water followed by 366 pounds of 45% sodium hydrosulfide and 291 pounds of benzyl chloride. One gallon of 31.5% hydrochloric acid was charged, and the reactor was heated to 50° C. An additional 1.5 gallons of hydrochloric acid was added in ca. 0.3 gallon increments spaced throughout the run. The reactor was held at 50° C. until the benzyl chloride was about 10 area percent by gas chromatography (about 6 hours). The temperature was then raised to 80° C. and held until the benzyl choride was less than 0.3 area percent (about 3 hours). The reactor agitator was then stopped and the heating water was turned off. The bottom brine phase was transferred out of the reactor, and the remaining organic product was water washed. The product phase was then transferred to a second vessel where it was dried by heating to 80° C. under 25 inches of vacuum. The resulting product weighed 285 pounds and was 97.5% by weight benzyl mercaptan.

From the benzyl mercaptan produced in accordance with the method of this invention can be produced S-benzyl thiolcarbamate, in accordance with the following procedure.

Preparation of Benzyl Chlorothioformate

A 100 ml flask was fitted with a magnetic stirrer, a thermometer, a gas inlet tube and a cold-finger condenser connected to a caustic scrubber. Benzyl mercaptan (20.0 g) and trimethylamine hydrochloride (0.04 g) were charged to the flask and heated to 50° C., and solid carbon dioxide and acetone were charged to the condenser. Phosgene (26 g) was added over 1 hour, and heating was continued for an ambient temperature to remove excess phosgene. The oily product (28.7 g, 98.6% of theory) was 97.2 weight percent benzyl chlorothioformate, <0.1% benzyl mercaptan, 0.1% benzyl chloride, 0.4% benzyl disulfide, and 0.1% benzyl dithiocarbonate.

Preparation of N,N-dipropyl-S-benzylthiocarbamate

A 250 ml flask was fitted with a magnetic stirrer, a thermometer, a gas inlet tube, and a pressure-equalizing addition funnel. The gas inlet tube was connected with a "T" to a nitrogen source and a caustic scrubber. The flask was placed under a nitrogen atmosphere and was charged with 60 ml of a 10% sodium hydroxide solution, 50 ml of toluene, and 15 ml of dipropylamine. Benzyl chlorothioformate (20 g) was added dropwise over a 5-minute period with cooling in an ice-water bath, and stirring was continued for an additional 30 minutes. The reaction mixture was washed once with 60 ml of warm water and twice with 60 ml of 3N hydrochloric acid solution. The organic phase was concentrated under reduced pressure to give 26.0 g of technical N,N-dipropyl-S-benzylthiocarbamate (98.65 of theory) which was 97.2 weight percent N,N-dipropyl-S-benzylthiocarbamate, 0.1 area percent benzyl chloride, 0.4% dipropylamine, 0.5% benzyl sulfide, 0.3% benzyl disulfide and 0.1 benzyl dithiocarbonate.

What is claimed is:

1. A method for the preparation of benzyl mercaptan which comprises reacting a benzyl halide of the formula

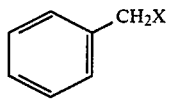

wherein X is chlorine or bromine, with an alkali metal hydrosulfide salt, at a temperature and for a sufficient period of time to cause formation of benzyl mercaptan, said reaction being conducted under a hydrogen sulfide atmosphere at a temperature of about 50° C. until approximately 90% of the starting material is converted to the benzyl mercaptan, then increasing the temperature to about 80° C. for the balance of the reaction, the inital concentration of said hydrosulfide salt in solution being between about 5% and about 30% weight.

2. The method of claim 1 wherein said hydrogen sulfide atmosphere is maintained by the addition of hydrochloric acid to the reaction solution.

3. The method of claim 1 wherein said benzyl halide is benzyl chloride.

4. The method of claim 1 wherein the initial concentration of hydrosulfide salt in solution is 15% by weight.

5. The method of claim 1 wherein said hydrosulfide salt is sodium hydrosulfide.

6. The method of claim 1 wherein said benzyl halide is benzyl bromide.

* * * * *